United States Patent [19]
Knuth et al.

[11] Patent Number: 5,814,487
[45] Date of Patent: Sep. 29, 1998

[54] USE OF AGARASE ENZYME TO ISOLATE NUCLEIC ACIDS

[75] Inventors: Mark W. Knuth, Waunakee; Susanne Selman, Madison, both of Wis.

[73] Assignee: Promega Corporation, Madison, Wis.

[21] Appl. No.: 799,552

[22] Filed: Feb. 13, 1997

Related U.S. Application Data

[63] Continuation-in-part of Ser. No. 655,704, Jun. 3, 1996.
[51] Int. Cl.$^6$ .................... C12P 19/44; C12P 19/14; C12N 9/24; C08B 1/00
[52] U.S. Cl. ................. 435/74; 435/99; 435/200; 435/274; 435/810
[58] Field of Search .............. 435/200, 18, 274, 435/74, 99, 810

[56] References Cited

U.S. PATENT DOCUMENTS 5,234,809   8/1993   Boom et al. ..................... 435/91.2

OTHER PUBLICATIONS

Morrice, Lora M.; McLean, Maitland W.; Long, William F. and Williamson, Frank B., β–Agarases I and II from *Pseudomonase atlantica*–Substrate specificities, *Eur. J. Biochem.* (1983) 137: 149–154.
Morrice, Lora M.; McLean, Maitland W.; Long, William F. and Williamson, Frank B., β–Agarases I and II from *Pseudomonas atlantica*–Purificatins and Some Properties, *Eur. J. Biochem.* (1983) 135: 553–558.
Belas, Robert; Bartlett, Douglas, and Silverman, Michael, Cloning and Gene Replacement Mutagenesis of a *Pseudomonas atlantica* Agarase Gene, *Applied and Environmental Microbilogy*, (Jan. 1988) 54:1, pp. 30–37.
Belas, Robert, Sequence Analysis of the agrA Gene Encoding β–Agarase from *Pseudomonas atlantica*, *Journal of Bacteriology*, (Jan. 1989) pp. 602–605.
Kadokami, Yoichi and Lewis, Randolph V., Reverse Electrophoresis to Concentrate DNA Fractions, *Analytical Biochemistry*, (1995), 226: pp. 193–195.
Gnirke, Andreas; Huxley, Clare; Peterson, Ken and Olson, Maynard V., Microinjection of Intact 200– to 500–kb Fragments of YAC DNA into Mammalian Cells, (1993), *Genomics*, 15: pp. 659–667.
Potier, M.–C.; Kuo, W.L.; Dutriaux, A.; Gray, J. and Geodert, M., Construction and Characterization of a Yeast Artificial Chromosome Library Containing 1.5 Equivalents of Human Chromosome 21, (1992), *Genomics*, 14: pp. 481–483.

Maule, John C.; Porteous, David J. and Brookes, Anthony J., An Improved Method for Recovering Intact Pulsed Field Gel Purified DNA, of at least 1.6 Megabases, (1994), *Nucleic Acids Research*, 22:15: pp. 3245–3246.
Gold, Paul, Use of a Novel Agarose Gel–Digesting Enzyme for Easy and Rapid Purification of PCR–Amplified DNA for Sequencing, (1992), *BioTechniques 133*, 13:1: pp. 132–134.
Belas, Robert; Bartlett, Douglas and Silverman, Michael, Cloning and Gene Replacement Mutagenesis of a *Pseudomonas atlantica* Agarase Gene, (Jan. 1988), *Applied and Environmental Microbiology*, pp. 30–37.
Epicentre Technologies Pubication, GELase™ Agarose Gel–Digesting Preparation Product Information, (Aug. 1993), 5 pages.
New England Biolabs Publication, β–Agarase I, (Apr. 1993), 3 pages.
Calbiochem® Biochemicals for Research, 121814 Agarase, *Pseudomonas atlantica*, p. 8.
FMC Corporation Publication, β–Agarase, 1 page.
Promega Technical Bulletin, Promega Corporation, Madison, Wisconsin, (Jun. 1995), pp. 1–17.
Knoche, Kimberly; Selman, Susanne; Kobs, Gary; Brady, Melinda and Knuth, Mark, Modifying Enzymes, (Oct. 1995), *Promega Notes Magazine*, 54: pp. 14–19.
Selman, Susanne; Knoche, Kim and Knuth, Mark, Modifying Enzymes, (Aug. 1995), *Promega Notes Magazine*, 53: pp. 6–11.
Zuklic, Frank W. (1992) *Characterization of Bacterial Marine Isolate NR19 and the Partial Purification of its Secreted Agarase* (Masters Degree Thesis submitted to the University of South Florida).
Southern, E.M., Long Range Periodicities in Mouse Satellite DNA, (1975), *J. Mol. Biol.* 94: pp. 51–69.
Blin, N. et al., Isolation of Large Molecular Weight DNA from Agarose Gels for Further Digestion by Restriction Enzymes, (Apr. 1975), *North Holland Publishing Co.* 53:1, pp. 84–86.
Vogelstein, Bert et al., Preparative and Analytical Purification of DNA from Agarose (Feb. 1979), *Proc. Natl. Acad. Sci.* 76:2, pp. 615–619.
Kin, N.M.K. et al., Properities of Agar; Parameters Affecting Gel–Formation and the Agarose–Iodine Reaction (1972), *Carbohydrate Res.* 25: pp. 379–385.

*Primary Examiner*—Robert A. Wax
*Assistant Examiner*—Elizabeth Slobodyansky
*Attorney, Agent, or Firm*—DeWitt Ross & Stevens SC

[57] ABSTRACT

A process for isolating nucleic acids from agarose, and particularly regular agarose, is described wherein the agarose is augmented with a chaotropic substance and hydrolyzed by a novel purified agarase enzyme from *Flavobacterium sp.* strain NR19.

21 Claims, 3 Drawing Sheets

USE OF AGARASE ENZYME TO ISOLATE NUCLEIC ACIDS

REFERENCE TO RELATED APPLICATIONS

The present application is a continuation-in-part of U.S. patent application Ser. No. 08/655,704, filled Jun. 3, 1996 entitled "ISOLATED AGARASE ENZYMES FROM *FLAVOBACTERIUM SP.* STRAIN NR19, CLONED GENES THEREFOR, AND EXPRESSION THEREOF IN TRANSFORMED HOST CELLS," which is incorporated herein by reference in its entirety.

FIELD OF THE INVENTION

The present invention relates generally to a process for isolating nucleic acids from agarose gels. More specifically, the present invention relates to a process and a kit for enzymatically isolating nucleic acids, such as DNA and RNA, from regular- or low-melting agarose using lower than normal melting temperatures.

DESCRIPTION OF THE PRIOR ART

Agarose, or more correctly agaroses, are widely used as gels in the electrophoretic separation of deoxyribonucleic acid (DNA) and ribonucleic acid (RNA). Agarose is capable of forming gels which allow DNA or RNA strands to be separated without destroying the activity of the DNA or RNA molecules. A highly heterogeneous polysaccharide, agarose is an alternating co-polymer of 3-linked β-D-galactopyranose and 4-linked 3,6-anhydro-α-L-galactopyranose.

To form an agarose gel for electrophoretic separation purposes, a hot solution of agarose is prepared. The hot agarose solution is cast in an electrophoresis apparatus and allowed to cool. As the solution cools, it reaches a loose gel state, i.e., the gelling point where agarose chains form double helices which join together to form loosely associated bundles or fibrils (the Gel I state). As the gel cools further still, the bundles further associate with each other to reach a point where a hardened agarose gel structure is formed (the Gel II state). It is this Gel II structure which is widely used in agarose gel electrophoresis (Kin, N. M. K. et al., 1972, *Carbohydrate Res.* 25: 379–385).

High purity agarose for gel electrophoresis is essentially a commodity item and is commercially available from a number of national suppliers. For instance, low melting point (LMP) Preparative Grade Agaroses are available from the Promega Corporation (Madison, Wis.). Similar agaroses can also be obtained from the FMC BioProducts Corporation (Rockland, Me.).

The conventional procedure for agarose gel electrophoresis begins by the casting of an agarose gel (Gel II) in a suitable electrophoresis chamber. Tris/acetate/EDTA buffer (TAE) or tris/borate/EDTA buffer TBE) is typically included in the molten gel solution. Then the DNA or RNA is loaded into the gel and electrophoresed. After the electrophoresis is complete and the band visualized by suitable means, a second procedure is begun to harvest the nucleic acids of interest from the agarose gel.

It is well known in the art to harvest nucleic acids from an agarose gel by physically excising the gel containing the DNA or RNA of interest from the remainder of the gel. A number of methods can then be employed to harvest the DNA/RNA from the gel. One commonly used method employs an agarase enzyme, which hydrolyses the gel and liberates the DNA/RNA. Conventional harvesting protocols using agarase enzymes proceed by first exchanging the electrophoresis buffer for an agarase enzyme reaction buffer more favorable for agarase activity. This buffer exchange is necessary because conventional agarase enzymes are generally less active in pH/salt conditions usually used for electrophoresis. Then the solid agarose gel is melted by heating to temperatures of approximately 65° to 100° C., depending on the type of agarose.

There are two basic types of agarose gels used for purification of DNA and RNA, often referred to as regular agarose (high melting) and low melting agarose. Low melting agarose used for DNA and RNA typically melts at 65°14 70° C., whereas regular agarose typically melts at 95°–100° C.

Because commercially available agarases will not digest unmelted agarose, it is currently necessary to melt the gel. This is thought to be due to the tight, interlocking nature of the agarose Gel II state, which sterically prohibits access of the agarase enzymes to the interior of the agarose chains. Unfortunately, temperatures above 75° C. may result in thermal degradation of the desired nucleic acid contained within the agarose rendering them unsuitable for subsequent applications. For this reason, only agaroses that melt at the lower temperatures (65°–70° C.) can be used for these applications.

Once the agarose has been completely melted, the gel is equilibrated at a lower temperature between about 42° to 45° C., the temperature at which the now commercially available agarase enzymes exhibit optimum agarose digesting activity. Once the gel has equilibrated at the proper temperature, agarase enzyme is added to the gel and allowed to digest the agarose into small neoagaro-oligosaccharide chains. Then the nucleic acids contained in the gel can be separated from the small oligosaccharide fragments of the digested gel by a variety of means, including ethanol precipitation.

A major drawback of this procedure is that two competing physical phenomena are at play. On the one hand, the gel must be melted at suitably high temperatures in order for the matrix to be completely disassociated so that the agarose chains are accessible to the agarase enzyme. However, at these high temperatures, agarase enzymes subsequently added to the gel are often adversely affected. For instance, if the agarase enzyme is added to the agarose too quickly after melting, the enzyme can be completely inactivated. On the other hand, if the agarose gel is allowed to equilibrate at a lower temperature for too long, the Gel I state can reform. Because the agarase enzyme cannot digest the re-formed gel, only partial digestion of the agarose gel is achieved. This results in incomplete recovery of the nucleic acids of interest. Thus, there is a strong motivation to carry out the enzyme digestion at a reasonably high temperature so as to inhibit gel re-formation while simultaneously avoiding thermal inactivation of the nucleic acid sample and the agarase enzyme itself.

Parent application Ser. No. 08/655,704, which is incorporated herein by reference, describes a novel purified agarase enzyme isolated from *Flavobacterium sp.* strain NR19, hereafter referenced as NR19 42 kD agarase enzyme, which exhibits a high level of agarase activity. This enzyme has a molecular weight of 42 kD by SDS-PAGE. NR19 42 kD agarase enzyme provides for the digestion of agarose electrophoresis gels using an enzyme which has fast hydrolysis rates, exhibits good thermal stability, and remains active at high pHs so as to eliminate for exchange buffers prior to initiating the digestion reaction.

NR19 42 kD agarase enzyme is typically used to harvest nucleic acids from agarose gels in situations where researchers do not want to use resin-based methods. The major limitation of NR19 42 kD agarase enzyme and all other agarases is that they currently require premelting of agarose to completely hydrolyze the gel. At the high temperatures required to melt regular agaroses, DNA and RNA can be damaged. For this reason, when most researchers use agarase enzymes to harvest DNA or RNA, they do so with low melting agaroses. However, regular agaroses offer a number of significant performance advantages not seen in low melting agaroses. For example, regular agarose typically gives superior electrophoretic resolution and has higher gel strength, making handling easier. Therefore, there is a need to combine the benefits of using a regular agarose with an agarase enzyme (such as NR19 42 kD agarase) to isolate nucleic acids, without a requirement for exposure to temperatures exceeding 70° C.

However, the novel NR19 42 kD agarase enzyme by itself has a difficult time isolating undamaged nucleic acids from certain forms of agarose gels, specifically regular agarose gels.

Therefore, there is a need to combine the benefits of a regular agarose with the novel NR19 42 kD agarase enzyme to isolate nucleic acids at lower temperatures.

SUMMARY OF THE INVENTION

The present invention is directed to a process for isolating nucleic acids from agarose, comprising adding a chaotropic substance to the agarose in a quantity sufficient to lower the melting temperature of the agarose to a range suitable for isolating and harvesting the nucleic acid; and adding a chaotrope-resistant agarase enzyme in a quantity sufficient to isolate the nucleic acid from the agarose. The preferred chaotrope-resistant agarase enzyme is NR19 42 kD agarase enzyme.

The present invention is further directed to isolating nucleic acids from regular agarose as above, wherein a sufficient quantity of chaotrope is added to lower the melting point of the agarose to between 65° and 70° C., heating the mixture to between 65° and 70° C. until the gel melts, diluting the melted agarose such that the chaotrope concentration can maintain the agarose in a melted state at reduced temperatures (typically at or about 37° C.) at which the NR19 42 kD agarase enzyme can function, lowering the temperature to about 37° C., and adding NR19 42 kD enzyme in a quantity sufficient to hydrolyze the agarose, thus enabling the isolation of the nucleic acid.

The present invention is further directed to a process for isolating nucleic acids from low melting agarose as above, wherein a sufficient quantity of chaotrope is added to lower the melting point of the agarose to between 35° and 40° C., heating the agarose to between 35° and 40° C. until the gel melts; diluting the melted agarose such that the chaotrope concentration can maintain the agarose in a melted state at reduced temperatures (typically at or around 37° C.) at which the NR19 42 kD agarase enzyme can function, adding NR19 42 kD agarase enzyme in a quantity sufficient to isolate the nucleic acid from the agarose; and isolating the nucleic acids from the agarose.

The present invention is further directed to hydrolyzing agarose under conditions described above without the express aim of isolating DNA or RNA.

The present invention is also directed to a kit for accomplishing the above referenced purposes, which contains NR19 42 kD agarase enzyme, a chaotropic solution consisting of sodium iodide (NaI) or potassium iodide (KI), an antioxidant such as sodium sulfite where necessary to prevent accumulation of free iodine, and instructions for use.

The invention is generally directed to the use of a chaotropic substance to depress the melting point of agaroses and an agarase enzyme, such as NR19 42 kD agarase enzyme, which exhibits good activity in the hydrolysis of agarose in the presence of the chaotropic substance at the effective concentration. This provides a new way of harvesting nucleic acids.

The resulting process has the advantages of being easy to use and quick, taking approximately two hours. The main advantage of using NR19 42 kD agarase enzyme to digest agarose in the presence of chaotropic salts is that the NR19 42 kD agarase enzyme allows the preparative use of regular agarose without subjecting it to temperatures over 70° C. where damage to DNA and RNA can occur. Further, NR19 42 kD agarase enzyme can use low melt agarose without subjecting it to temperatures over 37° C. which is advantageous to the handling and recovery of very large DNA particles or where extremely mild conditions are desired.

The advantage of the present invention over resin-based methods of DNA recovery is that the present system does not require operational steps which cause shearing of large DNA. Additionally, no transfer steps are required. Thus, the present invention can be referred to as a "one pot recovery system."

The objects and advantages of the invention will appear more fully from the following detailed description of the invention made in conjunction with the accompanying drawings.

The objects and advantages of the invention will appear more fully from the following detailed description of the preferred embodiment of the invention made in conjunction with the accompanying drawings.

DETAILED DESCRIPTION OF THE INVENTION

Figure 1:
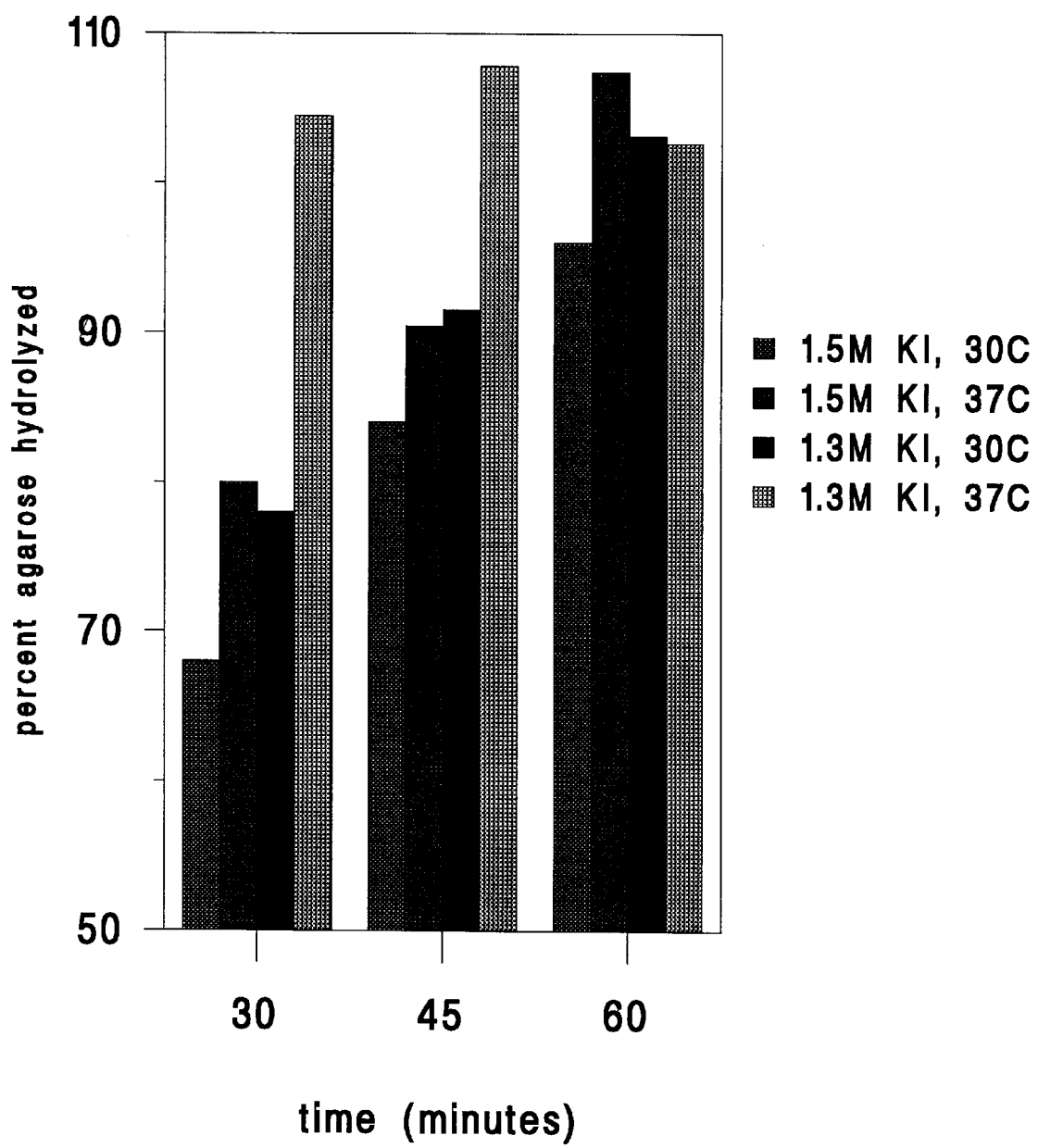
FIG. 1 is a histogram depicting the degree of agarose hydrolysis resulting from treatment with KI and digestion with NR19 42 kD agarase enzyme as a function of digestion time, temperature, and net concentration of KI.

The protocol of the present invention is based on the observed activity of NR19 42 kD agarase enzyme in high molarity solutions of KI or NaI and the following experimental observations:

1. It takes at least 2.2–2.5M of KI or NaI to completely melt 1% regular agarose in 1× TAE buffer in 15–25 minutes at 65° C., or to completely melt 1% low melting agarose in 1× TAE buffer in 15–25 minutes at 37° C.

2. It takes at least 2.2–2.5M of NaI to completely melt 1% regular agarose in 1× TBE buffer in 15–25 minutes at 65° C., or to completely melt 1% low melting agarose in 1× TBE buffer in 15–25 minutes at 37° C. KI will not work for depressing the melting point of agaroses in TBE buffer without adding additional excipients.

3. Stock solutions of KI and NaI can be prepared at ≦6M and ≦8M, respectively. This allows concentrations of these salts ≧2.2–2.5M to be achieved in agarose gel slices via the addition of relatively small quantities of these concentrated stock solutions.

4. NR19 42 kD agarase enzyme appears to reproducibly hydrolyze melted agarose in 1.3–1.5M KI/TAE at 30°–37° C. at 25–50% of the rate observed for melted agarose in TAE or TBE buffers at 47° C. It also appears to reproducibly hydrolyze melted agarose in 1.1–1.3M NaI/TAE or NaI/TBE at 30°–37° C. at ≧50–75% of the rate observed for melted agarose in TAE or TBE at 42°–47° C.

There are several interacting factors that are possibly responsible for the lowered optimal reaction temperature in the presence of KI or NaI. The first factor is the degree to which the agarose is retained in the fully melted form at temperatures lower than 42° C. In the presence of KI or NaI, this is probably maximized, allowing greater access of the enzyme to the agarose chains. The second factor is the degree to which KI and NaI depress the inactivation temperature of the enzyme itself. Inactivation of NR19 42 kD agarase enzyme begins to be observed at around 55°–60° C. in the absence of KI or NaI. This would be expected to drop significantly due to the chaotropic nature of these salts. To summarize, in the absence of KI or NaI, the enzyme may exhibit intrinsic activity at 37° C. equal or greater than that at 42°–47° C.; however at temperatures below 42° C., the agarose begins to regel, thus preventing enzyme access. In the presence of KI or NaI, the enzyme starts to become inactivated at 42°–47° C., however since the gel is maintained in a sufficiently melted state at lower temperatures (such as 37° C.) to allow enzyme access, the enzyme can be used at the lower temperatures where it still retains considerable intrinsic activity.

The basic component features of the present system are an agarose gel, chaotropic substances such as KI or NaI, and NR19 42 kD agarase enzyme. As stated previously, the agarose component may be low melt agarose or regular agarose. It is known that agarose gel can be dissolved readily in solutions of chaotropic salts such that nucleic acid bands from the gels may be recovered (U.S. Pat. No. 5,075,430 to Little). Known methods for recovering DNA from agarose with chaotropes all use either filtration, which is cumbersome, or resin binding, which can cause low recoveries of DNA less than 200 bp and shearing of DNA that is greater than 10 kbp.

Chaotropic substances disturb the structure of water such that the burying of hydrophobic residues within the internal structures of bioorganic polymers is no longer thermodynamically as favored as in water alone. This often results in the depression of the melting points of agaroses and the inactivation temperatures of enzymes. For this reason, concentrations of chaotropes sufficient to depress the melting points of agaroses could be very deleterious to the activity of agarase enzymes as well. Preferred chaotropic substances for the present invention include NaI and KI, which appear to be able to selectively depress the melting point of agarose without significantly inactivating NR19 42 kD agarase enzyme. The NR19 42 kD agarase enzyme is an example of a chaotrope-resistant agarase enzyme, which for the purpose of this document is defined as any agarolytic enzyme which retains at least 50% of the activity observed in optimal aqueous buffers when tested in 0.25× TBE buffer containing ≧1.1M NaI at 35°–45° C.

By nucleic acid is meant both DNA and RNA in any possible configuration, i.e., in the form of double-stranded nucleic acid or in the form of single-stranded nucleic acid, or as a combination. Without wishing to be restricted to any one form of nucleic acid, the rest of this disclosure will refer to DNA.

Gel Melting Step

The chaotropic substance, typically KI or NaI, is used to depress the melting temperature of regular agarose to 65°–70° C. and low melt agarose to around 37° C. In the former case, the temperature is low enough to prevent damage to most DNA, and in the latter case, to minimize damage to very large DNA.

Chaotropic salt solutions are added from a concentrated stock to a net concentration of approximately 2.2–2.6M, and gel is melted at the reduced temperatures noted above for at least 15 minutes. Preferably KI or NaI in the range of 2.2–2.6M are used, from a stock solution at 5.8–7.0M. The solution should be protected from light, and if trace iodine is detected (faint brown color), sodium sulfite can be added until the color just disappears. The optimal time for the melting stage is generally between 20 and 30 minutes.

Gel Digestion Step

The digestion step is accomplished at an optimal temperature of 35°–39° C. and at about 1.3–1.5M KI or 1.1–1.3M NaI. These salt and approximate temperature ranges are easily attained by addition of an equal volume of water at or slightly below room temperature. Under these conditions, it has been found that NR19 42 kD agarase enzyme operates to hydrolyze the agarose gel whereas the current commercial agarases generally do not work in KI and work poorly in NaI. At this temperature range, which is slightly lower than that for the agarase enzyme alone (in the absence of the chaotropic substance), the agarose is kept molten, but remains hydrolyzable and accessible to the enzyme.

Operation

A protocol for harvesting DNA or RNA from regular agarose gels is as follows. For the purposes of illustration, the volume ratios are kept simple; however for processing of the maximum size of gel slice in a given tube size, more concentrated chaotrope stocks can be used. The protocol for low melting agarose is identical, except the melting and digestion steps are both at 37° C.:

1. add 1 volume of 4.4M NaI to the gel;
2. heat at 65° C. for 15–30 minutes;
3. once the gel has melted, add one volume of water, place in a 37° C. bath and add one unit of NR19 42 kD agarase enzyme per 200 mg 1% gel for 30 minutes;
4. add coprecipitant if desired (30 ug glycogen suggested);
5. add two volumes of 100% EtOH at room temperature for 30 minutes to 2 hours;
6. centrifuge the solution for 15 minutes at high speed (14,000–16,000×g) in a microcentrifuge at room temperature;
7. wash the resulting pellet in cold 70% EtOH and dry; and
8. reconstitute the pellet in water.

The resultant DNA or RNA should then be ready for use in a variety of applications. The EtOH precipitation removes most of the contaminating KI or NaI, which remains in the supernatant and wash.

**The unit concentration is defined as follows: 1 unit of agarase enzyme completely hydrolyzes 200 mg of 1% agarose in 1× TBE buffer in 15 minutes at 42°–47° C. (Promega Catalog, Part No. M1741).

Kits

The present invention also contemplates the formation of a kit. The kit includes a container with a sufficient quantity of NR19 42 kD agarose, a container with a chaotropic substance sufficient to lower the melting point of agarose to a desired level, and instructions for use.

The quantities of the various reagents in the kit can be varied depending on a number of factors, such as the optimum sensitivity of the process. The instructions for use are suitable to enable a researcher to obtain nucleic acid that is usable for subsequent applications.

EXAMPLES

The invention will now be illustrated by a number of examples. The following examples are presented to illustrate the advantages of the present invention and to assist one of ordinary skill in making and using the same. The examples are not intended in any way to otherwise limit the scope of the disclosure or protection granted by the patent.

Example 1
Effects of KI and NaI on Agarose Melting Temperature 100 ul aliquots of 1% SEAKEM GTG agarose (FMC BioProducts Corporation, Rockland, Me.) in 1× TAE were prepared. Then 1–4 volumes of KI at stock concentrations of 1–4M were added, and samples were incubated at 65° C. for 15–25 minutes. After 15 and 25 minutes, samples were removed and scored visually for presence of unmelted agarose. After comparing the scores with the net concentrations of KI in the samples, it was found that all samples containing $\geq$2 2.25M KI were completely melted after 15 minutes, with a few samples between 2 and 2.25M being completely melted after 25 minutes. When similar agarose was prepared in the presence of 1× TBE, concentrations of KI up to 4M were not able to cause the agarose to melt at 65°–70° C. Parallel experiments with NaI in place of KI yielded very similar melting results, with the exception that NaI did work in the presence of 1× TBE buffer.

Example 2
Preliminary Evidence of NR19 42 kD Agarase Enzyme Activity in KI

100ul aliquots of 1% SEAKEM GTG agarose in 1× TAE were prepared. Then 2 volumes of 4M KI were added (net KI concentration 2.6M), and samples were incubated at 65° C. for 30 minutes. Next, samples were transferred to a 44° C. bath, and 0, 0.5, 1, and 2 units of NR19 42 kD agarase enzyme were added. After the samples were incubated for 15 minutes, 600 ul EtOH were added. Then the samples were spun 10 minutes at 16,000×g in a microcentrifuge. The supernatants were removed, and 0.5 ml of 0.2N HCl were added. The tubes were capped and heated to 100° C. for 5 minutes to completely hydrolyze any precipitated agarose (not hydrolyzed by the enzyme). 25 ul aliquots of the hydrolysate were assayed for reducing sugar (indicative of agarose unhydrolyzed by the enzyme) as described in Dygert, S. et al., 1965, *Anal. Biochem.* 13: 367. Whereas the samples untreated with the agarase enzyme yielded 18.8 umol reducing sugar/ml (0% hydrolyzed), samples treated with 0.5, 1, and 2 units of agarase enzyme yielded 6%, 34% and 100% hydrolyzed, respectively. This was the earliest indication that the enzyme had activity in chaotropic solutions such as KI or NaI.

Example 3
Determination of Effects of Time, Temperature and KI Concentration on Effectiveness of NR19 42 kD Agarase Activity 100 ul aliquots of 1% SEAKEM GTG agarose in 1× TAE were prepared. Then 2 volumes of 4M KI were added (net KI concentration 2.6M), and samples were incubated at 65° C. for 30 minutes. Next, various samples were transferred to baths at 30° or 37° C.; $H_2O$ was added to make net concentration of KI either 1.3 or 1.5M, then 1 unit of NR19 42 kD agarase enzyme was added. Samples were taken from all reactions at 30, 45, and 60 minutes, then analyzed for ethanol precipitable agarose as described in Example 2 above. Controls verified that 100% of the original undigested agarose could be precipitated with ethanol in 1.3–1.5M KI. The percentage ethanol precipitable agarose was calculated in comparison to the value obtained for a similarly diluted undigested sample. This value was then used to calculate the percent agarose hydrolyzed. FIG. 1 presents the results of the experiment, which shows the percent agarose hydrolyzed as a function of time at two temperatures (30° and 37° C.) by two concentrations of KI (1.3 and 1.5M). The results clearly indicate that the effective hydrolysis conditions are a function of time (in this case 60 minutes is preferable), concentration of KI (in this case, 1.3M KI is preferable), and temperature (in this case, 37° C. is preferable). Note that in this case, 1 unit of enzyme is able to hydrolyze 100 ul of 1% agarose in $\leq$30 minutes; this represents a retention of at least 25% of the optimal activity (as noted in the unit activity definition described earlier).

Using the information presented in this application and the process of optimization described in this experiment, users skilled in the art are able to determine optimal temperatures, times, chaotrope concentrations, and enzyme amounts for any other agarose (such as low melting agarose), or chaotrope (such as NaI). In experiments similar to the one described above, optimal conditions for digestion using NaI were investigated; it was found that at between 1.1 and 1.3M NaI and 30°–37° C., NR19 42 kD agarase enzyme retained over 75% of its optimum activity. It was also determined that the same protocol could be used to melt low melting agarose at 37° C. in 2.2–2.6M NaI and to hydrolyze it at 37° C. in solutions containing 1.1–1.3M NaI.

Example 4
Demonstration of Unique Chaotrope Resistance of NR19 42 kD Agarase Enzyme 100 ul aliquots of 1% SEAKEM GTG agarose in 1× TAE were prepared. Then a concentrated stock of NaI was added to 2.2M and samples were incubated at 65° C. for 30 minutes. Next, water was added to each sample to a net NaI concentration of 1.1M, and samples were transferred to 37° C. bath. Next, 0.3–3 units (determined by assaying the vendors' enzymes under standard conditions as described in the Operation protocol, supra.) of the following agarase enzymes were added:

NR19 42 kD agarase "Promega"** enzyme;
"FMC" agarase (FMC Corporation, Rockland, Me.; originally from Epicentre, Madison, Wis.);
"NEB" beta agarase (New England Biolabs, Beverly, Mass.);
"BMB" agarase (Boehringer Mannheim, Indianapolis, Ind.); and
"CBC" beta agarase I (Calbiochem, San Diego, Calif.).

Figure 2:
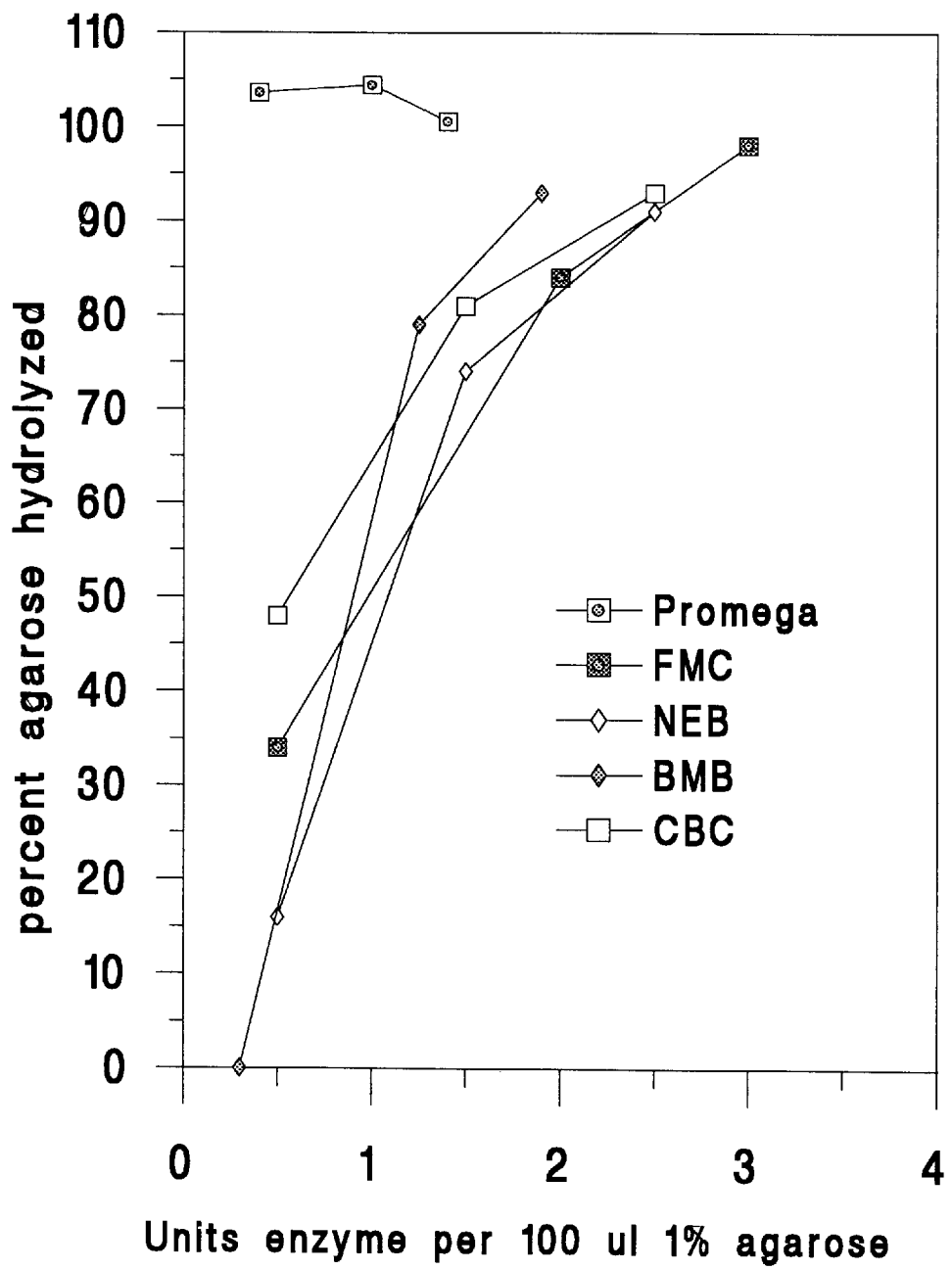
FIG. 2 is a graph depicting the degree of agarose hydrolysis resulting from treatment with NaI and digestion with NR19 42 kD agarase enzyme versus various amounts of other commercially available agarase enzymes.

** Names and abbreviations within quotations ("") refer to referenced lines on FIG. 2.

Samples were incubated 30 minutes. Then the samples were precipitated and pellets assayed as in Example 2. As presented in FIG. 2, the NR19 42 kD Promega agarase enzyme completely hydrolyzed the agarose at 0.4–1.4 units of enzyme per 100 ul 1% agarose. 0.4 U of the NR19 42 kD Promega agarase enzyme corresponds to $\geq$63% retention of activity. The other enzymes tested were much less efficient at agarose hydrolysis. Even in the best case (BMB), the required amount of enzyme for complete hydrolysis is at least 4 and more likely 8 times greater than for NR19 42 kD agarase enzyme.

Example 5
Sample Protocol for NR19 42 kD Agarase Enzyme Digestion of Regular Melt Agarose Using KI 80 ul slices of 1% SEAKEM GTG agarose in 1× TAE buffer containing 20 ng DNA (pGEM 3Zf(+)) (Promega Catalog, Part No. P2271) were prepared.

The following stock solutions were prepared:
1. 5.2M KI (86.5 g KI (Sigma P4286, Sigma Chemical, St. Louis, Mo.) dissolved in 100 ml water)
2. 2.2 mg/ml sodium sulfite (Sigma S8018)
3. 3 ug/ml glycogen: (30 mg glycogen (Sigma) dissolved in 10 ml water, diluted 1:1000 and sterile filtered)

KI stock solution was visually inspected for lack of brown color (free iodine). If there was color, 1/100–1/1000 volume of sodium sulfite was added until the solution was colorless. To each gel slice 80 ul of 5.2M KI was added. The gel slice was heated to 65°–70° C. for 15–30 minutes with occasional agitation until the agarose completely melted.

NR19 42 kD agarase enzyme was diluted just before use in cool deionized water (4°–15° C.) at a ratio of 4.5 ul NR19 42 kD (1 unit) per 160 ul water. The sample was removed from the high temperature heater, and 165 ul of diluted enzyme was added to the melted gel. The sample was vortexed vigorously and placed at 37° C. for 30–45 minutes. The sample was removed from the low temperature heater and 10 ul of 3 ug/ml glycogen and 690 ul EtOH was added.

The sample was vortexed and centrifuged at maximum speed for 15 minutes at room temperature. The supernatant was decanted and the pellet was washed 1–2× with 1 ml cold 70% EtOH. The pellet was dried and reconstituted in a desired volume of water.

The above-referenced process resulted in a DNA recovery of 88%–92% (multiple tests), a residual oligosaccharide of –6% and a residual KI≦about 80 nmoles with 1 wash.

Figure 3:
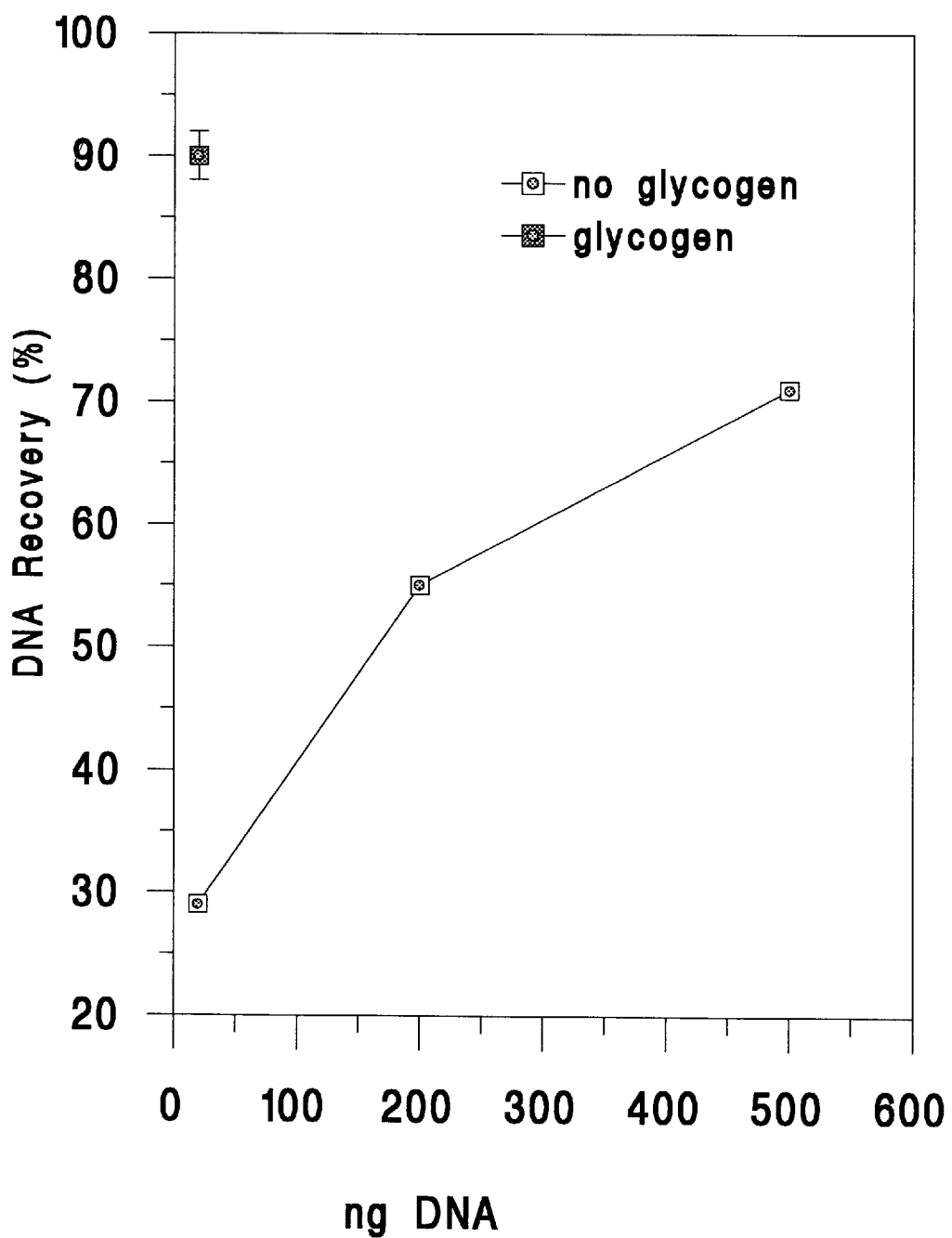
FIG. 3 is a graph of the quantity of DNA recoverable using NR19 42 kD agarase enzyme in the presence of KI, followed by ethanol precipitation with or without glycogen carrier, as a function of DNA quantity.

Example 6
Demonstration that DNA can be Recovered from Hydrolyzed Agarose Gels Using Agarase Enzyme/KI Agarose samples were prepared, digested with agarase enzyme, and precipitated as per the optimal KI conditions in Example 3, with the exception that 20–500 ng of pGEM3zf (+) plasmid were added to agarose before hydrolysis. After precipitation, samples were reconstituted in a volume of water equivalent to the original gel volume and assayed for DNA using SYBR Green 1 Dye (FMC Corp), using the original plasmid stock as a concentration standard. Results are presented in FIG. 3. Recoveries were >50% at DNA concentrations ≧200 ng per gel slice. As noted in Example 5 and indicated on the graph (even though it was a separate experiment) addition of 0.3% glycogen prior to EtOH precipitation resulted in recoveries around 90%, even for levels of DNA in the 20 ng range.

It is understood that the invention is not confined to the particular construction and arrangement of parts herein illustrated and described, but embraces such modified forms thereof as come within the scope of the following claims.

What is claimed is:

1. A process for isolating nucleic acids from agarose, comprising:
   a. adding a chaotropic substance to the agarose in a quantity sufficient to lower the melting temperature of the agarose to a range suitable for isolating and harvesting the nucleic acids; and
   b. adding an agarase enzyme to the agarose in a quantity sufficient to isolate the nucleic acids from the agarose.

2. The process of claim 1 wherein the agarase enzyme is NR19 42 kD agarase enzyme.

3. The process of claim 1 wherein the agarose is regular agarose and the melting temperature is lowered to between 65° C. and 70° C.

4. The process of claim 1 wherein the agarose is low melt agarose and the melting temperature is lowered to about 37° C.

5. The process of claim 1 wherein the chaotropic substance is at least one compound selected from the group consisting of sodium iodide and potassium iodide.

6. The process of claim 1 wherein the chaotropic substance is sodium iodide.

7. The process of claim 1 wherein the nucleic acid is DNA or RNA.

8. A process for hydrolyzing agarose comprising:
   lowering the melting point of the agarose by adding a chaotropic substance to the agarose to yield an agarose-chaotrope mixture; and
   hydrolyzing the agarose-chaotrope mixture by adding an agarose enzyme thereto.

9. The process of claim 8 wherein the agarose is regular agarose and wherein the melting point of the agarose is lowered to between 65° C. and 70° C.

10. The process of claim 8 wherein the agarose is low melt agarose and the melting point of the agarose is lowered to about 37° C.

11. A process for isolating nucleic acids from regular agarose, comprising:
   a. forming a chaotrope-agarose solution by adding a chaotropic substance to the agarose in a quantity sufficient to lower the melting point of the chaotrope-agarose solution to a range suitable for isolating and harvesting the nucleic acids, wherein the range of melting points is between 65° C. and 70° C.;
   b. heating the chaotrope-agarose solution to a temperature between 65° C. and 70° C.;
   c. diluting the chaotrope-agarose solution sufficiently to maintain the chaotrope-agarose solution in a melted gel state at about 37° C.;
   d. lowering the temperature of the chaotrope-agarose solution to about 37° C.;
   e. adding NR19 42 kD agarase enzyme to the chaotrope-agarose solution in a quantity sufficient to isolate the nucleic acids from the agarose; and
   f. isolating the nucleic acids from the agarose.

12. The process of claim 11 comprising adding an antioxidant to the chaotropic substance.

13. The process of claim 11 wherein the antioxidant is sodium sulfite.

14. The process of claim 11 wherein the chaotropic substance is at least one compound selected from the group consisting of sodium iodide and potassium iodide.

15. The process of claim 11 wherein the chaotropic substance is sodium iodide.

16. The process of claim 11 wherein the nucleic acid is DNA or RNA.

17. A kit for isolating nucleic acids from agarose comprising agarase enzyme, a chaotropic substance in quantities sufficient to lower the melting temperature of the agarose to a range suitable for isolating and harvesting the nucleic acids, and instructions for use.

18. The kit of claim 17 wherein the chaotropic substance is at least one compound selected from the group consisting of sodium iodide and potassium iodide.

19. The kit of claim 17 wherein the chaotropic substance is sodium iodide.

20. The kit of claim 17 further comprising an antioxidant in an amount sufficient to prevent accumulation of free iodine.

21. The kit of claim 20 wherein the antioxidant is sodium sulfite.

* * * * *